US011911136B2

United States Patent
Agell et al.

(10) Patent No.: US 11,911,136 B2
(45) Date of Patent: Feb. 27, 2024

(54) SYSTEM AND METHOD FOR CALCULATING CARDIAC PULSE TRANSIT OR ARRIVAL TIME INFORMATION

(71) Applicant: Stichting IMEC Nederland, Eindhoven (NL)

(72) Inventors: Carlos Agell, Eindhoven (NL); Evelien Hermeling, Soerendonk (NL); Vojkan Mihajlovic, Eindhoven (NL)

(73) Assignee: IMEC Nederland, Eindhoven (NL)

( * ) Notice: Subject to any disclaimer, the term of this patent is extended or adjusted under 35 U.S.C. 154(b) by 683 days.

(21) Appl. No.: 16/901,385

(22) Filed: Jun. 15, 2020

(65) Prior Publication Data

US 2020/0390348 A1 Dec. 17, 2020

(30) Foreign Application Priority Data

Jun. 17, 2019 (EP) .................................... 19180537

(51) Int. Cl.
| | |
|---|---|
| *A61B 5/021* | (2006.01) |
| *A61B 5/0225* | (2006.01) |
| *A61B 5/00* | (2006.01) |
| *A61B 5/0205* | (2006.01) |
| *A61B 5/318* | (2021.01) |

(52) U.S. Cl.
CPC ........ *A61B 5/02125* (2013.01); *A61B 5/0205* (2013.01); *A61B 5/0225* (2013.01); *A61B 5/02116* (2013.01); *A61B 5/318* (2021.01); *A61B 5/4803* (2013.01); *A61B 5/7203* (2013.01); *A61B 5/725* (2013.01); *A61B 5/7228* (2013.01); *A61B 5/7253* (2013.01)

(58) Field of Classification Search
CPC ...... A61B 5/02125; A61B 5/4803; A61N 5/06
See application file for complete search history.

(56) References Cited

FOREIGN PATENT DOCUMENTS

WO 2020092786 A1 5/2020

OTHER PUBLICATIONS

Yang, Chenxi, and Negar Tavassolian. "Pulse transit time measurement using seismocardiogram, and in-ear acoustic sensor." 2016 IEEE Biomedical Circuits and Systems Conference (BioCAS). pp. 188-191.

(Continued)

*Primary Examiner* — Yingchuan Zhang
*Assistant Examiner* — Jessica L Mullins
(74) *Attorney, Agent, or Firm* — McDonnell Boehnen Hulbert & Berghoff LLP

(57) ABSTRACT

A device for calculating a subject's cardiac pulse transit or arrival time information is configured to receive an electronic audio signal with information indicative of a human voice signal and a primary cardiac pulse signal; generate a power spectral profile of a section of the electronic audio signal, and detect a fundamental frequency (F0) of the generated power spectral profile; generate a denoised audio signal; generate a time-domain intermediate signal that captures frequency, amplitude and/or phase of the denoised audio signal; detect at least one intermediate signal fiducial point, within a human cardiac band, in the intermediate signal; detect at least one primary cardiac pulse fiducial point, within a human cardiac band, in the primary cardiac pulse signal; calculate pulse transit time or pulse arrival time information between the at least one detected primary cardiac signal fiducial point and the at least one detected intermediate signal fiducial point.

19 Claims, 11 Drawing Sheets

(56) References Cited

OTHER PUBLICATIONS

Extended European Search Report and Written Opinion, EP Application No. 20180451.5, dated Nov. 4, 2020, 11 pages.
Yang, Chenxi, and Negar Tavassolian. "Pulse transit time measurement using seismocardiogram and in-ear acoustic sensor." In 2016 IEEE Biomedical Circuits and Systems Conference (BioCAS), pp. 188-191. IEEE, 2016.
Orlikoff, Robert F., and R. J. Baken. "Fundamental frequency modulation of the human voice by the heartbeat: preliminary results and possible mechanisms." The Journal of the Acoustical Society of America 85, No. 2 (1989): 888-893.
Orlikoff, Robert F., and R. J. Baken. Abstract of "Fundamental frequency modulation of the human voice by the heartbeat: preliminary results and possible mechanisms." The Journal of the Acoustical Society of America 85, No. 2 (1989): 1-1.
Scanlon, Michael V. "Acoustic sensors in the helmet detect voice and physiology." In Sensors, and Command, Control, Communications, and Intelligence (C3I) Technologies for Homeland Defense and Law Enforcement II, vol. 5071, pp. 41-51. International Society for Optics and Photonics, 2003.
Khandelwal, Saransh, Simrat Sahni, Sanjeev Kumar, and Amod Kumar. "Pressure Sensor Based Estimation of Pulse Transit Time." International Journal of Information & Computation Technology 4 (2014): 1321-1328.
Schuller, Bjorn, Felix Friedmann, and Florian Eyben. "Automatic recognition of physiological parameters in the human voice: Heart rate and skin conductance." In 2013 IEEE International Conference on Acoustics, Speech and Signal Processing, pp. 7219-7223. IEEE, 2013.
Mesleh, Abdelwadood, Dmitriy Skopin, Sergey Baglikov, and Anas Quteishat. "Heart rate extraction from vowel speech signals." Journal of computer science and technology 27, No. 6 (2012): 1243-1251.

SYSTEM AND METHOD FOR CALCULATING CARDIAC PULSE TRANSIT OR ARRIVAL TIME INFORMATION

CROSS-REFERENCE TO RELATED APPLICATIONS

The present application is a non-provisional patent application claiming priority to European Patent Application No. 19180537.3, filed Jun. 17, 2019, the contents of which are hereby incorporated by reference.

FIELD OF THE DISCLOSURE

The present description relates generally to electronic systems for calculating cardiac pulse transit time (PTT) or pulse arrival time (PAT) information and more specifically to an electronic system for calculating cardiac pulse transit/arrival time using a primary cardiac pulse signal and an electronic audio signal input.

BACKGROUND

Continuous, non-invasive and cuff-less estimation of arterial blood pressure (BP) gained emerging interest for health care applications. Instead of commonly used cuff-based measurements, changes in the Pulse Wave Velocity (PWV), i.e., the speed of a pressure pulse propagating along the arterial wall, can be an alternative approach for a continuous, non-invasive and indirect BP measurement. As a surrogate of PWV, an indirect estimation of BP can also be obtained with the use of Pulse Transit Time (PTT) or Pulse Arrival Time (PAT). PWV can be computed as a ratio between the distance the pulse travels and the transit/arrival times (PTT or PAT). Pulse transit time methods can also be used as proxy measurements for arterial stiffness. Therefore, there is an increasing interest for PTT/PAT calculation techniques that can be used as a cardiovascular variable or as an indicator for blood pressure (both systemic and pulmonary) and arterial stiffness. An example technique is disclosed in "Pulse Transit Time Measurement using Seismocardiogram and In-Ear Acoustic Sensor" by C. Yang et al., 2016 IEEE Biomedical Circuits and Systems Conference (BioCAS), pp. 188-191, 2016.

There is a motivation to improve the current state of the art electronic systems and methods for non-invasive calculation of cardiac pulse transit or arrival times.

SUMMARY

A new and improved system and method for non-invasively calculating cardiac pulse transit or arrival time information are proposed herein, which allow calculating a subject's cardiac pulse transit or arrival time using a primary cardiac pulse signal recorded from the subject (used as a time reference for the pulse) and fiducial points detected in an electronic audio signal generated by the subject. According to example embodiments, the electronic system can calculate a subject's cardiac pulse transit or arrival time using calculations in the time-domain. According to an example embodiment, the electronic system makes use of synchronized voice and cardiac signals for calculating pulse arrival time information. According to an example embodiment, the electronic system can process cardiac signals preserving the phases of the signal (or relative phases). According to an example embodiment, the electronic system can process the audio and cardiac signal and provide PTT/PAT information in real-time, while the subject is generating the audio signal. According to an example embodiment, the electronic system can process the audio and cardiac signal and provide PTT/PAT information beat by beat. According to example embodiments, additional statistics can be computed based on the beat by beat information (e.g., average N beats to provide a more robust output). According to an example embodiment, the electronic system provides for asynchronous demodulation of the audio signal based on the fundamental frequency of a vowel audio sound. According to an example embodiment, the system can automatically adapt to different subjects' voices, thus avoiding the need for training configuration phases. According to an example embodiment, the method herein described exposes hard to measure cardiovascular parameters. According to an example embodiment, the solution can be implemented in a wearable sensor or integrated into a distributed electronic device network. Another example embodiment can be implemented as a software solution on, for example, a smartphone or an offline system based on recorded (but synchronized) signals.

According to an example embodiment, there is provided an electronic system for calculating a subject's cardiac pulse transit time or pulse arrival time information using a primary cardiac pulse signal and an electronic audio signal, wherein the electronic audio signal comprises information representative of a human voice signal in the time-domain, the human voice signal comprising a vowel audio sound of a certain duration and a fundamental frequency; and wherein the electronic system comprises: a signal receiving module configured for receiving the electronic audio signal and the primary cardiac pulse signal, wherein the electronic audio signal and the primary cardiac pulse signal are synchronized time-domain signals; an audio processing module configured for generating a power spectral profile of a section of the electronic audio signal, and for detecting the fundamental frequency of the generated power spectral profile; a denoising module configured for filtering the received audio signal within a band around at least the detected fundamental frequency and thereby generating a denoised audio signal; a signal transformation module configured for generating a time-domain intermediate signal that captures frequency, amplitude and/or phase of the denoised audio signal; a beat detection module configured for detecting at least one intermediate signal fiducial point, within a human cardiac band, in the intermediate signal; a primary cardiac pulse beat detection module configured for detecting at least one primary cardiac pulse fiducial point, within a human cardiac band, in the primary cardiac pulse signal; a cardiac pulse transit/arrival time module configured for calculating pulse transit time or pulse arrival time information between the at least one detected primary cardiac signal fiducial point and the at least one detected intermediate signal fiducial point.

According to an example embodiment, the signal source is the heart, and the timing is from the first signal to be generated in time (the primary cardiac pulse signal) to the electronic audio signal (which receives the pulse later). According to an example embodiment, if the primary cardiac pulse signal is an ECG signal, the outcome is pulse arrival time (PAT). According to example embodiments, if the primary pulse is a PPG or ICG signal, the outcome would be pulse transit time (PTT).

According to an example embodiment, the signal transformation module is configured for receiving the denoised audio signal and calculating the Hilbert transform, the complex autocorrelation with M samples delay, and the instantaneous frequency, thereby generating a time-domain intermediate signal capturing the frequency of the denoised audio signal.

According to an example embodiment, the signal transformation module is configured for generating an in-phase and quadrature signal of the denoised audio signal, with a carrier having a frequency that is the fundamental frequency; and calculating the $L^2$ norm of the in-phase and quadrature signals, thereby generating a time-domain intermediate signal capturing the amplitude of the denoised audio signal.

According to an example embodiment, the signal transformation module is configured for generating an in-phase and quadrature signal of the denoised audio signal, with a carrier having a frequency that is the fundamental frequency; and calculating the phase of the in-phase and quadrature signals, thereby generating a time-domain intermediate signal capturing the phase of the denoised audio signal.

According to an example embodiment, the denoising module is further configured for filtering the received audio signal also within bands around one or more multiples of the detected fundamental frequency and for generating one or more denoised audio signals.

According to an example embodiment, the denoising module is configured for generating a plurality of denoised audio signals, and the signal transformation module is configured for combining calculation results from each of the denoised audio signals.

An example embodiment relates to an electronic device comprising the electronic system for calculating cardiac pulse transit or arrival time information of a subject according to embodiments herein described.

An example embodiment relates to a method for, in an electronic system or device, calculating cardiac pulse transit or arrival time information of a subject, between a primary cardiac pulse signal and an electronic audio signal, wherein the electronic audio signal comprises information representative of a human voice signal in the time-domain, the human voice signal comprising a vowel audio sound of a certain duration and a fundamental frequency; and the method comprising: receiving the electronic audio signal and the primary cardiac pulse signal, wherein the electronic audio signal and the primary cardiac pulse signal are synchronized time-domain signals; generating a power spectral profile of a section of the electronic audio signal, and detecting the fundamental frequency of the generated power spectral profile; filtering the received audio signal within a band around at least the detected fundamental frequency and thereby generating a denoised audio signal; generating a time-domain intermediate signal that captures frequency, amplitude and/or phase of the denoised audio signal; and detecting at least one intermediate signal fiducial point within a human cardiac band in the intermediate signal; detecting at least one primary cardiac pulse fiducial point within a human cardiac band in the primary cardiac pulse signal; calculating pulse transit or arrival time information between the at least one detected primary cardiac signal fiducial point and the at least one detected intermediate signal fiducial point.

According to an example embodiment, the step of generating a time-domain intermediate signal that captures the frequency of the denoised audio signal comprises: calculating a Hilbert transform; calculating a complex autocorrelation with M samples delay, and calculating the instantaneous frequency.

According to an example embodiment, the step of generating a time-domain intermediate signal that captures amplitude of the denoised audio signal comprises: generating an in-phase and a quadrature signal of the denoised audio signal, with a carrier having a frequency that is the fundamental frequency; and calculating the $L^2$ norm of the in-phase and quadrature signals.

According to an example embodiment, the step of generating a time-domain intermediate signal that captures the phase of the denoised audio signal comprises: generating an in-phase and a quadrature signal of the denoised audio signal, with a carrier having a frequency that is the fundamental frequency; and calculating the phase of the in-phase and quadrature signals.

An example embodiment relates to a computer program product comprising computer program code means adapted for calculating cardiac pulse transit or arrival time information of a subject, according to the methods herein described when the program is run on a computer, and to a computer-readable storage medium comprising such computer program.

BRIEF DESCRIPTION OF THE FIGURES

The above, as well as additional features, will be better understood through the following illustrative and non-limiting detailed description of example embodiments, with reference to the appended drawings.

All the figures are schematic, not necessarily to scale, and generally only show parts that are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

In the description of various example embodiments that follows, various features may be described as being grouped together in a single embodiment, figure, or description thereof for the purpose of streamlining the disclosure and aiding in the understanding of one or more of the various aspects of the disclosure. This, however, should not be interpreted as a requirement that all the features are required. For example, particular embodiments may include those features recited in the claims. Furthermore, combinations of features of different embodiments are understood to fall within the scope of the claims, as would be clearly understood by those skilled in the art. In some instances, certain methods, structures, and techniques have not been shown in detail in order not to obscure the conciseness of the description.

Figure 1:
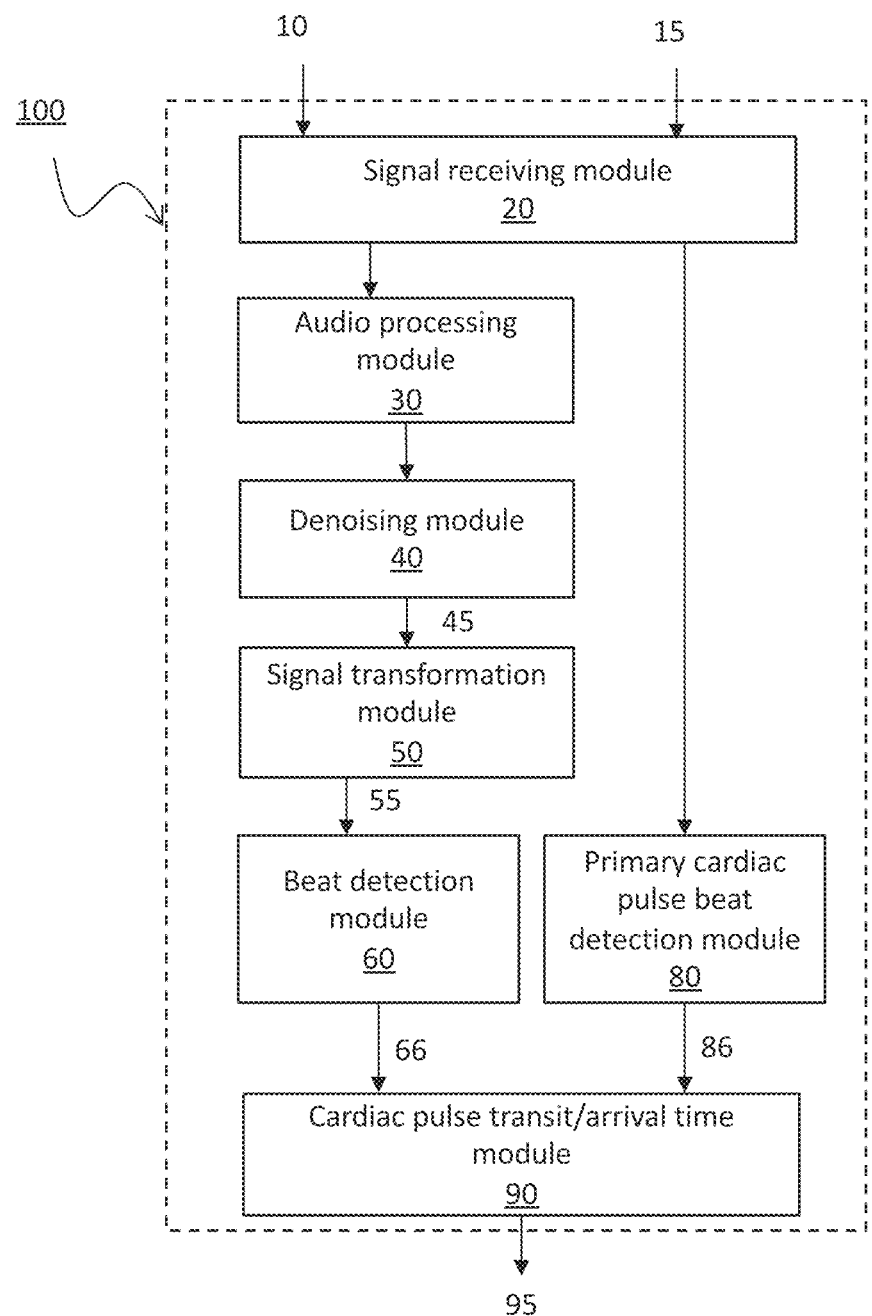
FIG. 1 shows a first general block diagram of an example system for calculating cardiac pulse transit or arrival time information, in accordance with an embodiment.

FIG. 1 shows a first general block diagram of an example system 100 for calculating cardiac pulse transit/arrival time information between a primary cardiac pulse signal 15 and an electronic audio signal 10. The system comprises a signal receiving module 20, an audio processing module 30, a denoising module 40, a signal transformation module 50, a beat detection module 60, a primary cardiac pulse beat detection module 80, and a cardiac pulse transit/arrival time module 90. In the following description, according to some examples, calculating pulse transit time information may be understood as calculating PTT and/or PAT information.

The electronic audio signal 10 comprises information representative of a subject's voice signal in the time-domain. The subject's voice signal comprises a vowel audio sound of a certain duration and a fundamental frequency (F0 in FIG. 4). In some embodiments, the electronic audio signal 10 may comprise a vowel audio sound that the subject has to sustain for a certain period or a vowel sound that is extracted from the subject's speech (e.g., by recognizing a vowel sound that has a certain duration or by stitching a plurality of vowel sounds). According to example embodiments, the electronic audio signal 10 may comprise a vowel audio sound having a certain minimum duration so as to comprise a detectable fundamental frequency characteristic of that subject. The electronic audio signal 10 may be a real-time signal or may be a non-real-time recorded signal that can also be post-processed with a latency or in non-real-time.

The electronic primary cardiac pulse signal 15 comprises information representative of the subject's cardiac pulse in the time-domain. According to example embodiments, the electronic cardiac pulse signal may be an electrocardiogram signal (ECG), an impedance cardiogram signal (ICG), a cardiac ultrasound signal recorded by an echogram or sonogram, a heart sound signal from a stethoscope sensor, a photoplethysmogram signal (PPG), an impedance plethysmogram signal (IPG), a speckle plethysmogram signal (SPG), or a pressure signal from a piezo sensor. According to example embodiments, the electronic primary cardiac pulse signal 15 may be a real-time signal or may be a non-real-time recorded signal that can also be post-processed with a latency or in non-real-time. According to example embodiments, the electronic cardiac pulse signal is used as a source timing reference for the computation of transit/arrival times with respect to the electronic audio signal 10.

The signal receiving module 20 is configured for receiving the electronic audio signal 10, e.g., from an audio sensor or transducer, such as for example a microphone, and the electronic primary cardiac pulse signal 15, e.g., from ECG electrodes connected to the subject's body. In some embodiments, the signal receiving module 20 may comprise wired or wireless transmission/receiving means to receive such electronic signals. In some embodiments, the signal receiving module 20 may comprise a storage or memory in which such electronic audio signals are temporarily or permanently stored. In some embodiments, the signal receiving module 20 may just comprise means for reading the electronic signals from a memory or storage unit. In example embodiments, the electronic audio signal is an analog or digital audio signal in the kHz range. In some example embodiments, the signal receiving module 20 may comprise analog to digital conversion, and audio signal conditioning means. According to some embodiments, the signal receiving module 20 receives the electronic audio signal and the primary cardiac pulse signal in a synchronized manner, that is, wherein the electronic audio signal and the primary cardiac pulse signal are synchronized in the time-domain. According to some example embodiments, the synchronization between the primary cardiac pulse signal and the audio signal is performed in hardware, meaning that the digitizing circuits for both signals share the same clock. In some example embodiments, when each of the digitizing circuits receives a sample (or a reduced group of samples) the digitizing circuit also collects the timestamp, which has a common clock source for both signals. According to some example embodiments, even if using an independent clock for each of the signals, a software-based synchronization may also be performed.

The audio processing module 30 is configured for generating a power spectral profile of a section of the electronic audio signal 10 and detecting the fundamental frequency (F0 in FIG. 4) of the generated power spectral profile. According to an example embodiment, a small portion of the voice is extracted from the electronic audio signal 10, and from the electronic audio signal 10, a power spectral profile is computed (see FIG. 4). According to example embodiments, from the power spectral profile, around the first peak detected is considered the fundamental frequency of the voice signal. According to example embodiments, the audio processing module 30 may also be configured for calculating or detecting subsequent harmonics of the fundamental frequency, located at around 2, 3, 4, . . . N times the fundamental frequency.

The denoising module 40 is configured for filtering the received audio signal within a band around at least the detected fundamental frequency and thereby generating a denoised audio signal 45. According to example embodiments, the denoising unit performs a bandpass filtering of the electronic audio signal 10 around the fundamental frequency F0 to reduce the sources of noise and avoid aliasing. According to example embodiments, the bandpass filtering can be done up to about +/−10 Hz around the fundamental frequency. According to example embodiments, the denoising module may be further configured for filtering the received electronic audio signal 10 also within bands around one or more harmonics or multiples of the detected fundamental frequency (2F0, 3F0, NF0 in FIG. 4) and for generating one or more denoised audio signals. According to example embodiments, the bandpass filtering can also be done up to about +/−10 Hz around the harmonics. For example, according to example embodiments, the denoising module 40 may generate a first denoised audio signal for the fundamental frequency and a second denoised audio signal for one of the corresponding harmonics. The denoising module 40 may also generate denoised audio signals for each of the harmonics (e.g., bandpass filtering the electronic audio signal 10 around the harmonic NF0, wherein N is an integer number). According to example embodiments, the denoising module may generate one denoised audio signal by bandpass filtering of the electronic audio signal 10 around the fundamental frequency F0 and around one or more harmonics.

The signal transformation module 50 is configured for generating a time-domain intermediate signal 55 that captures frequency, amplitude, and/or phase of the generated denoised audio signal 45. According to example embodiments, the signal transformation module may be configured for calculating the Hilbert transform of the denoised audio signal, the complex autocorrelation with M samples delay, and the instantaneous frequency, thereby generating a time-domain intermediate signal capturing the frequency of the denoised audio signal. According to example embodiments, the signal transformation module may be configured for generating an in-phase and quadrature signal of the denoised audio signal, with a carrier having a frequency that is the fundamental frequency, and calculating the $L^2$ norm of the in-phase and quadrature signals over time, thereby generating a time-domain intermediate signal capturing the amplitude of the denoised audio signal. According to example embodiments, the signal transformation module may be configured for generating an in-phase and quadrature signal of the denoised audio signal, with a carrier having a frequency that is the fundamental frequency; and calculating the phase of the in-phase and quadrature signals, thereby generating a time-domain intermediate signal capturing the phase of the denoised audio signal. According to example embodiments, when the denoising module 40 is configured for generating a plurality of denoised audio signal 45 corresponding to the detected fundamental frequency and one or more harmonics, the signal transformation module is configured for combining calculated results from each of the denoised audio signals.

The beat detection module 60 is configured for detecting at least one intermediate signal fiducial point 66 within a human cardiac band in the intermediate signal 55. According to example embodiments, the human cardiac band is around 40 to 200 bpm or 0.6 Hz to 3.5 Hz. According to example embodiments, the beat detection module is configured for detecting heartbeat information within a human cardiac band in the intermediate signal on the time-domain. According to example embodiments, the beat detection module is configured for extracting at least a time fiducial point from the intermediate signal 55, which is representative of the subject's heartbeat. According to some embodiments, such detected fiducial points may be based on peak detection in the signal or its derivatives, zero crossings, or other time-domain fiducial points. According to embodiments, the beat detection module 60 is configured for detecting a plurality of intermediate signal fiducial points, representative of beat by beat information of the subject's heartbeats. According to example embodiments, the beat detection module may be configured for performing a bandpass filtering of the intermediate signal around a human cardiac band.

The primary cardiac pulse beat detection module 80 is configured for detecting at least one primary cardiac pulse fiducial point 86 within a human cardiac band, in the primary cardiac pulse signal 15. According to example embodiments, the human cardiac band is around 40 to 200 bpm or 0.6 Hz to 3.5 Hz. According to example embodiments, the primary cardiac pulse beat detection module is configured for detecting cardiac pulse information, within a human cardiac band, on the time-domain. According to example embodiments, the primary cardiac pulse beat detection module is configured for extracting at least a time fiducial point from the cardiac pulse signal 15, which is representative of the subject's heartbeat. According to some examples, when the cardiac pulse signal 15 is an ECG signal, the primary cardiac pulse beat detection module may be configured for detecting R peak fiducial points. According to some examples, when the cardiac pulse signal 15 is an ICG signal, the primary cardiac pulse beat detection module may be configured for detecting B fiducial points. According to example embodiments, the beat detection module may be configured for performing a bandpass filtering of the intermediate signal around a human cardiac band.

The cardiac pulse transit/arrival time module 90 is configured for calculating pulse transit time information 95 between at least one of the detected primary cardiac signal fiducial points 86 and at least one of the detected intermediate signal fiducial points 66. According to example embodiments, the cardiac pulse transit/arrival time module 90 is configured for calculating a time difference between at least one detected primary cardiac signal fiducial point and at least one detected intermediate signal fiducial point corresponding to the same subject's heartbeat. According to example embodiments, the cardiac pulse transit/arrival time module 90 is configured for receiving timing information about a plurality of detected fiducial points from the primary cardiac pulse signal and the intermediate signal and for calculating timing differences (PTT/PAT) for a plurality of the subject's heart beats, e.g., one PTT/PAT value per beat. According to example embodiments, the cardiac pulse transit/arrival time module 90 may also calculate statistically filtered (e.g., mean or median) PTT/PAT values.

According to example embodiments, the system 100 for calculating cardiac pulse transit time information is configured for removing transition sections (e.g., start and end of audio signal recordings) when calculating transit/arrival times.

According to example embodiments, the system 100 for calculating cardiac pulse transit time information is configured for accounting for and compensating any delays, either systematic (setup dependent) or introduced by the system while processing the electronic audio signal 10 and the primary cardiac pulse signal 15. According to example embodiments, systematic delays may include hardware, software, and/or measurement principle delays. For example, measurement principle additive time offset can come from the time the voice needs to travel the distance between the vocal cords and the microphone collecting audio (in which voice travels at the speed of sound). System-introduced delays include processing delays, for instance, when signals are filtered.

Figure 2A:
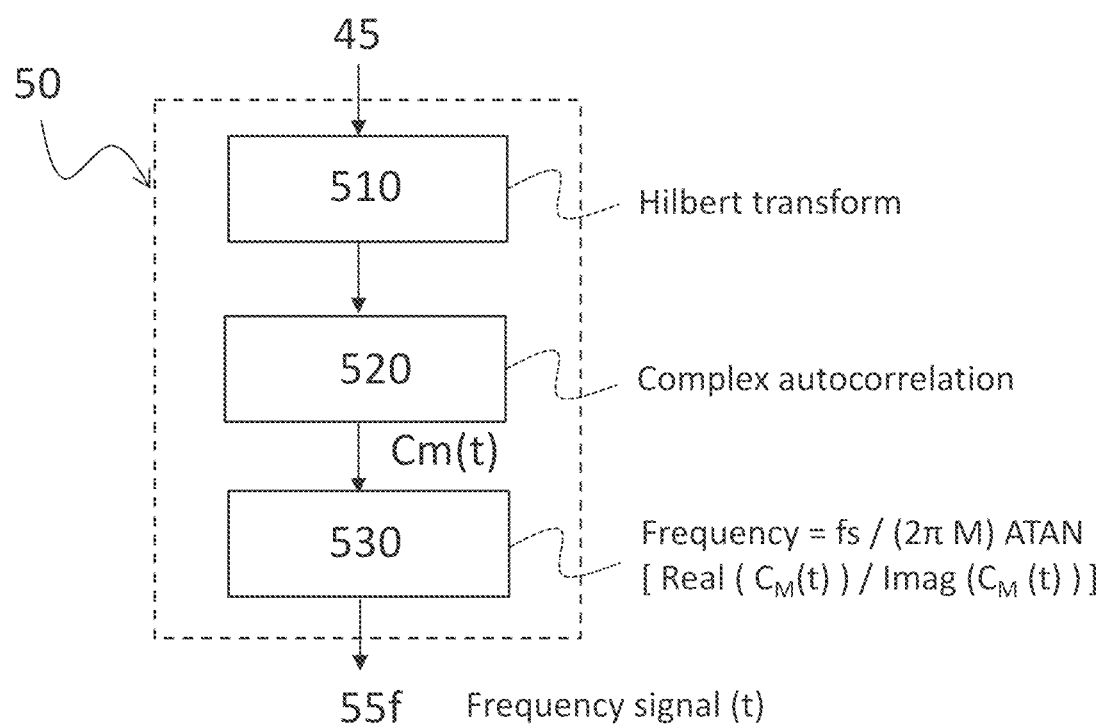
FIG. 2A shows a block diagram of a first example signal transformation module, in accordance with an embodiment.

FIG. 2A shows a block diagram of a first example signal transformation module 50 configured for generating a time-domain intermediate signal 55f that captures the frequency of the generated denoised audio signal 45. According to example embodiments, the signal transformation module includes a first block 510 configured to calculate the Hilbert transform of the received denoised audio signal, a second block 520 configured to calculate the complex autocorrelation of the Hilbert transform with M samples delay CM(t), a third block 530 configured to calculate the instantaneous frequency and low pass filter the instantaneous frequency signal to avoid aliasing. According to example embodiments, the signal transformation module 50 may further be configured for downsampling the instantaneous frequency signal, which may be utilized for real-time operation processing. According to example embodiments, the down-sampling is done to a human cardiac-like sampling frequency, e.g., 256 Hz.

Figure 2B:
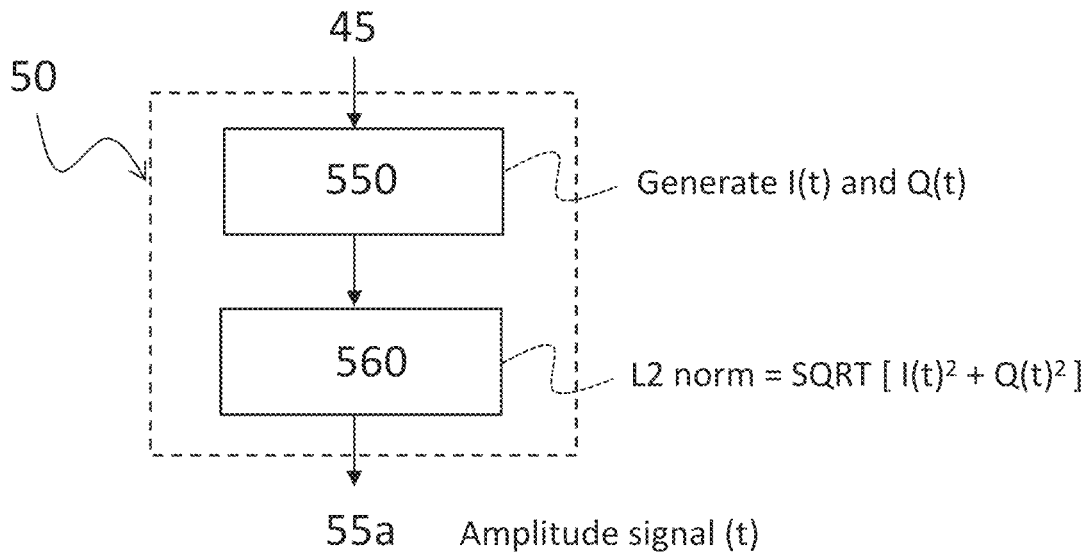
FIG. 2B shows a block diagram of a second example signal transformation module, in accordance with an embodiment.

FIG. 2B shows a block diagram of a second example signal transformation module 50 configured for generating a time-domain intermediate signal 55a that captures the amplitude of the generated denoised audio signal 45. According to example embodiments, the signal transformation module includes a first block 550 configured for generating an in-phase I(t) and quadrature Q(t) signal of the denoised audio signal, with a carrier having a frequency that is the fundamental frequency and a second block 560 configured for calculating the $L^2$ norm of the in-phase and quadrature signals. According to example embodiments, the signal transformation module is configured for: generating a sine wave having the fundamental frequency, and multiplying the denoised audio signal by the sine wave, thereby generating the in-phase signal I(t); generating a cosine wave having the fundamental frequency, and multiplying the denoised audio signal by the cosine wave, thereby generating the quadrature signal Q(t); and calculating the sample-by-sample square root of the sum of the squares of the in-phase and quadrature signals over time. According to example embodiments, the signal transformation module 50 may further be configured for low pass filtering and/or downsampling the in-phase I(t) and/or the quadrature signal Q(t), which may be useful for avoiding aliasing or for real-time operation processing. According to example embodiments, the down-sampling is done to a human cardiac-like sampling frequency, e.g., 256 Hz.

Figure 2C:
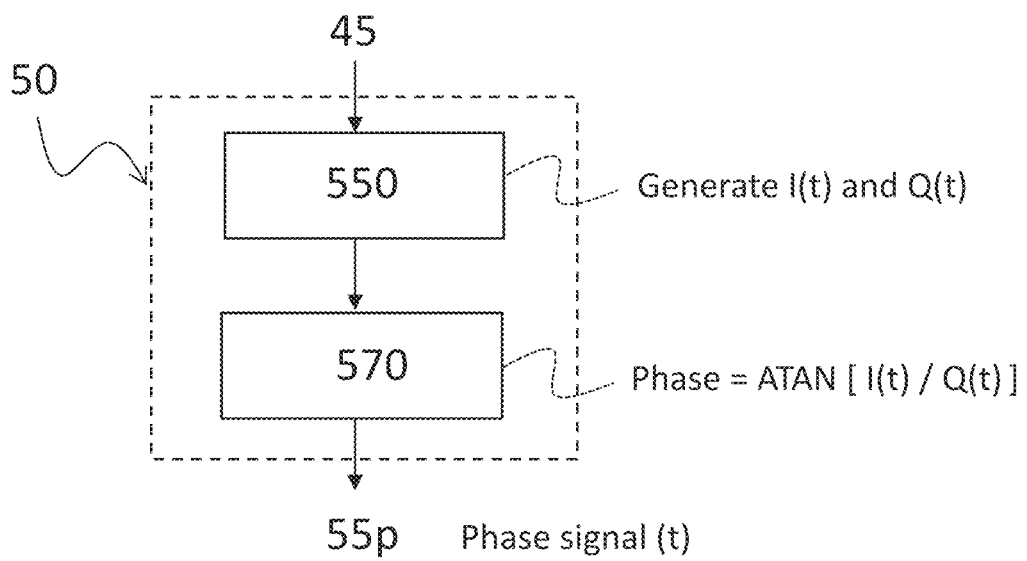
FIG. 2C shows a block diagram of a third example signal transformation module, in accordance with an embodiment.

FIG. 2C shows a block diagram of a third example signal transformation module 50 configured for generating a time-domain intermediate signal 55p that captures the amplitude of the generated denoised audio signal 45. According to example embodiments, the signal transformation module includes a first block 550 configured to generate an in-phase I(t) and quadrature Q(t) signal of the denoised audio signal, with a carrier having a frequency that is the fundamental frequency, and a second block 570 configured to calculate the phase of the in-phase and quadrature signals. According to example embodiments, the signal transformation module is configured for: generating a sine wave having the fundamental frequency, and multiplying the denoised audio signal by the sine wave, thereby generating the in-phase signal I(t); generating a cosine wave having the fundamental frequency, and multiplying the denoised audio signal by the cosine wave, thereby generating the quadrature signal Q(t); and calculating the arctangent of the in-phase signal divided by the quadrature signal. According to example embodiments, the signal transformation module may be configured for compensating the phase by 2 pi shifts in order to enforce signal continuity. According to example embodiments, the signal transformation module 50 may further be configured for low pass filtering and/or downsampling the in-phase I(t) and/or the quadrature signal Q(t), which may be useful for avoiding aliasing or for real-time operation processing. According to example embodiments, the down-sampling is done to a human cardiac-like sampling frequency, e.g., 256 Hz.

Figure 3:
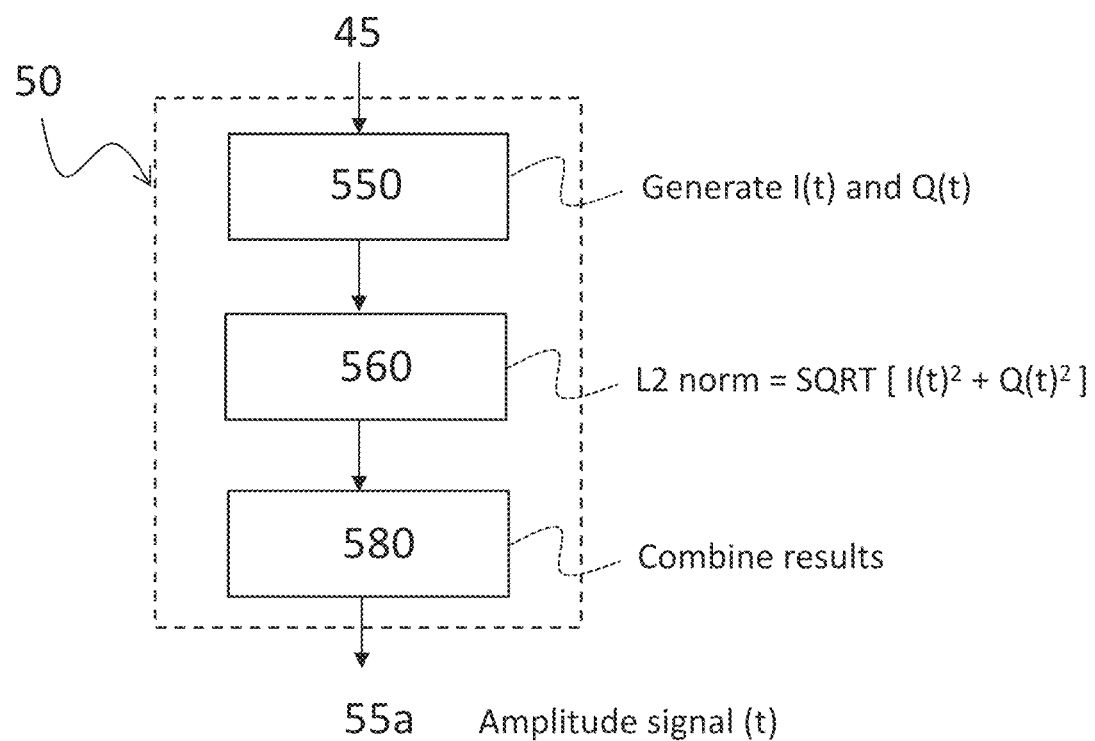
FIG. 3 shows a block diagram of a fourth example signal transformation module, in accordance with an embodiment.

FIG. 3 shows a block diagram of a fourth example signal transformation module 50 configured for generating a time-domain intermediate signal 55a that captures the amplitude of a plurality of generated denoised audio signal 45. According to example embodiments, the signal transformation module includes a first block 550 configured to generate an in-phase I(t) and quadrature Q(t) signal for each of a plurality of denoised audio signals (e.g., one corresponding to the fundamental frequency and at least another one corresponding to one harmonic), with a carrier having a frequency that is the fundamental frequency, a second block 560 configured to calculate the modulus of the in-phase and quadrature signals, and a third block 580 configured to combine calculated amplitude results from each of the denoised audio signals. According to example embodiments, the signal transformation module is configured for: generating an in-phase I(t) and quadrature Q(t) signal for each of a plurality of denoised audio signals (e.g., one corresponding to the fundamental frequency and at least another one corresponding to one harmonic), with a carrier having a frequency that is the fundamental frequency; combining generated in-phase I(t) and quadrature Q(t) signal values for each of the denoised audio signals; and calculating the modulus of the combined in-phase and quadrature signals.

Although FIG. 3 shows an example for a signal transformation module 50 configured for generating a time-domain intermediate signal 55a that captures the amplitude of a plurality of generated denoised audio signals 45, similar combinations can be done for a signal transformation module 50 configured for generating a time-domain intermediate signal 55p that captures the phase of a plurality of generated denoised audio signals 45. According to example embodiments, the signal transformation module is configured for: combining the received denoised audio signals; calculating the Hilbert transform of the combined audio signals; calculating the complex autocorrelation with M samples delay CM(t); calculating the instantaneous frequency, and low pass filtering the instantaneous frequency signal. According to example embodiments, the signal transformation module is configured for: calculating the Hilbert transform of each of the received denoised audio signals; calculating the complex autocorrelation with M samples delay CM(t) of each of the received denoised audio signals; calculating the instantaneous frequency for each of the CM(t); combining the instantaneous frequencies and low pass filtering the instantaneous frequency signal.

Figure 4:
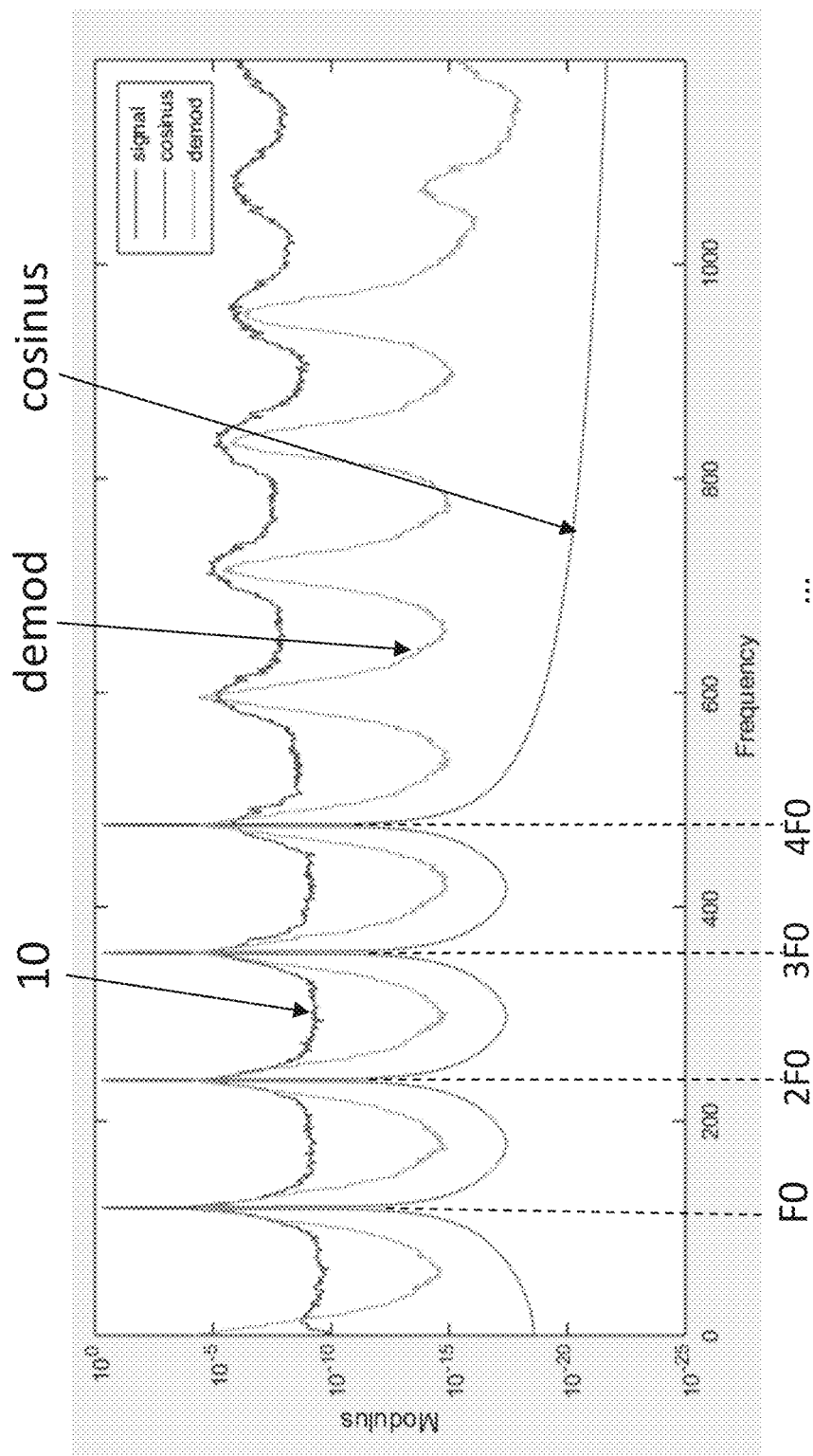
FIG. 4 illustrates a graph of an example electronic audio signal comprising a vowel audio sound having a fundamental frequency, in relation to other signals generated by the electronic system based on that fundamental frequency, in accordance with an embodiment.

FIG. 4 illustrates a graph of an example electronic audio signal 10 in the frequency domain, comprising a vowel audio sound having a fundamental frequency F0, and a plurality of harmonics 2F0, 3F0, 4F0, . . . NF0. In a further example, demodulation signals generated by the signal transformation module 50 are also shown together with the synthetically generated cosine signal with frequencies F0 and a plurality of harmonics 2F0, 3F0, 4F0 used in the demodulation process. It shall be noted that the frequency content of the input signal at the DC level is low to non-existing, whereas the demodulated signal levels in the DC area reflects the contents of the bands around the harmonics in the input signal. Such bandwidth contains the cardiac information to be decoded.

Figure 5:
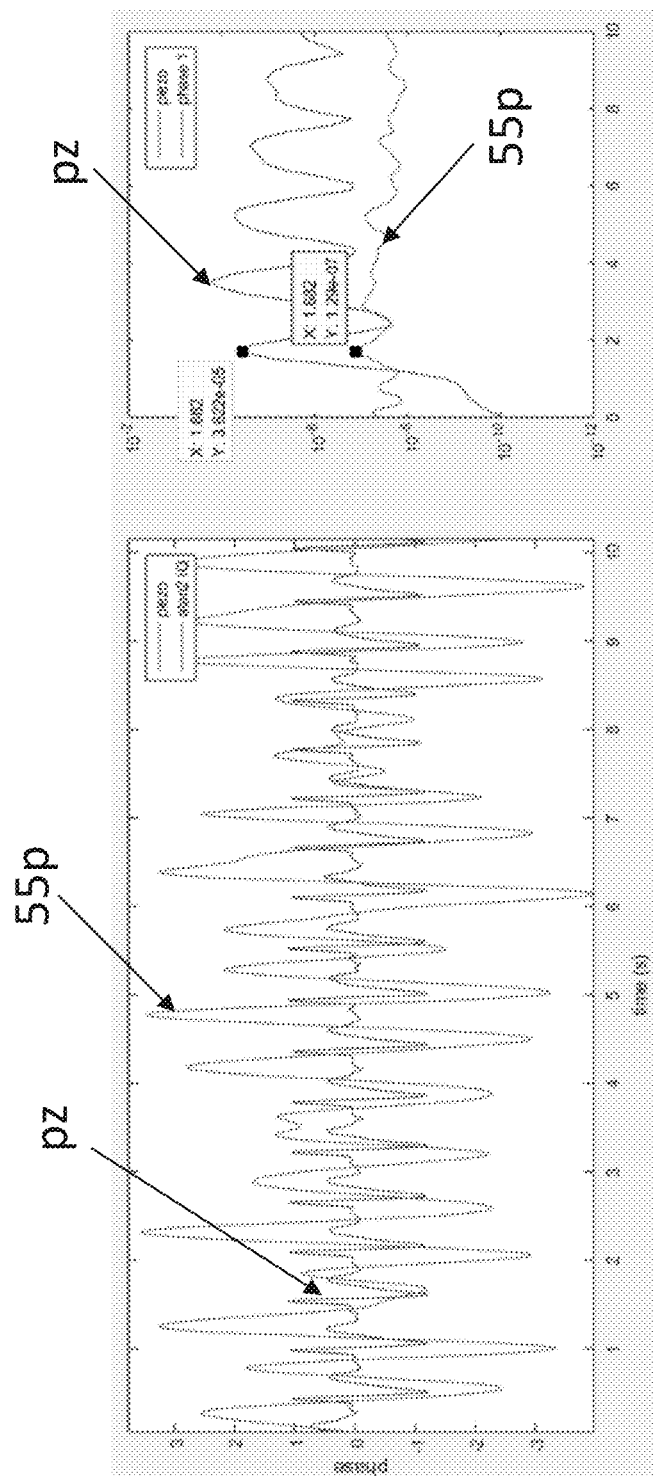
FIG. 5 illustrates a graph of an example time-domain intermediate signal with phase information, generated by the signal transformation module, and the comparison of the intermediate signal and a primary cardiac pulse signal in the frequency domain, showing the same location of the first harmonic, in accordance with an embodiment.

FIG. 5 illustrates a graph, in time-domain (left) and frequency domain (right), of an example intermediate signal

55p with phase information, generated by the signal transformation module 50. The intermediate signal 55p is compared with a primary cardiac pulse signal, pz, from a piezo-based sensor in the thumb measuring volumetric displacement. The time-domain graph (left) shows how the pulsatility of the signal 55p is similar to that of the primary cardiac pulse piezo signal, pz. The frequency-domain signal (right) reflects that the fundamental frequency of both the signals 55p (highest frequency peak) and reference pz (first peak) are in the exact same frequency location.

According to example embodiments, the signal transformation beat detection module 60 may provide information based on any of the time-domain intermediate signals 55 generated by the signal transformation module 50. According to example embodiments, the signal transformation beat detection module 60 may provide multiple information based on a plurality of time-domain intermediate signals 55f, 55a, 55p generated by the signal transformation module 50. According to example embodiments, the signal transformation beat detection module 60 may provide information based on a weighted or quality-related values derived from a plurality of time-domain intermediate signals 55f, 55a, 55p. In consequence, according to example embodiments, the cardiac pulse transit/arrival time module 90 may, therefore, provide pulse transit/arrival time information based on any of the time-domain intermediate signals 55 generated by the signal transformation module 50. According to example embodiments, the cardiac pulse transit/arrival time module 90 may provide multiple pulse transit/arrival time information based on a plurality of time-domain intermediate signals 55f, 55a, 55p generated by the signal transformation module 50. According to example embodiments, the cardiac pulse transit time module 90 may provide pulse transit/arrival time information based on a weighted or quality-related values derived from a plurality of time-domain intermediate signals 55f, 55a, 55p.

It shall be noted that the system 100 for calculating cardiac pulse transit/arrival time information according to embodiments of the invention may be implemented according to hardware and/or software state of the art techniques, comprising, for example, a microprocessor, microcontroller or digital signal processor that can understand and execute software program instructions. Some programmable hardware logic, ASIC, and/or memory means may be specifically designed also for executing the method or parts of it according to example embodiments of the invention. The system may be implemented in an electronic device. The electronic device may be a wearable or a tethered device. The system may work in real-time, almost real-time (with a latency) or in post-processing.

Figure 6:
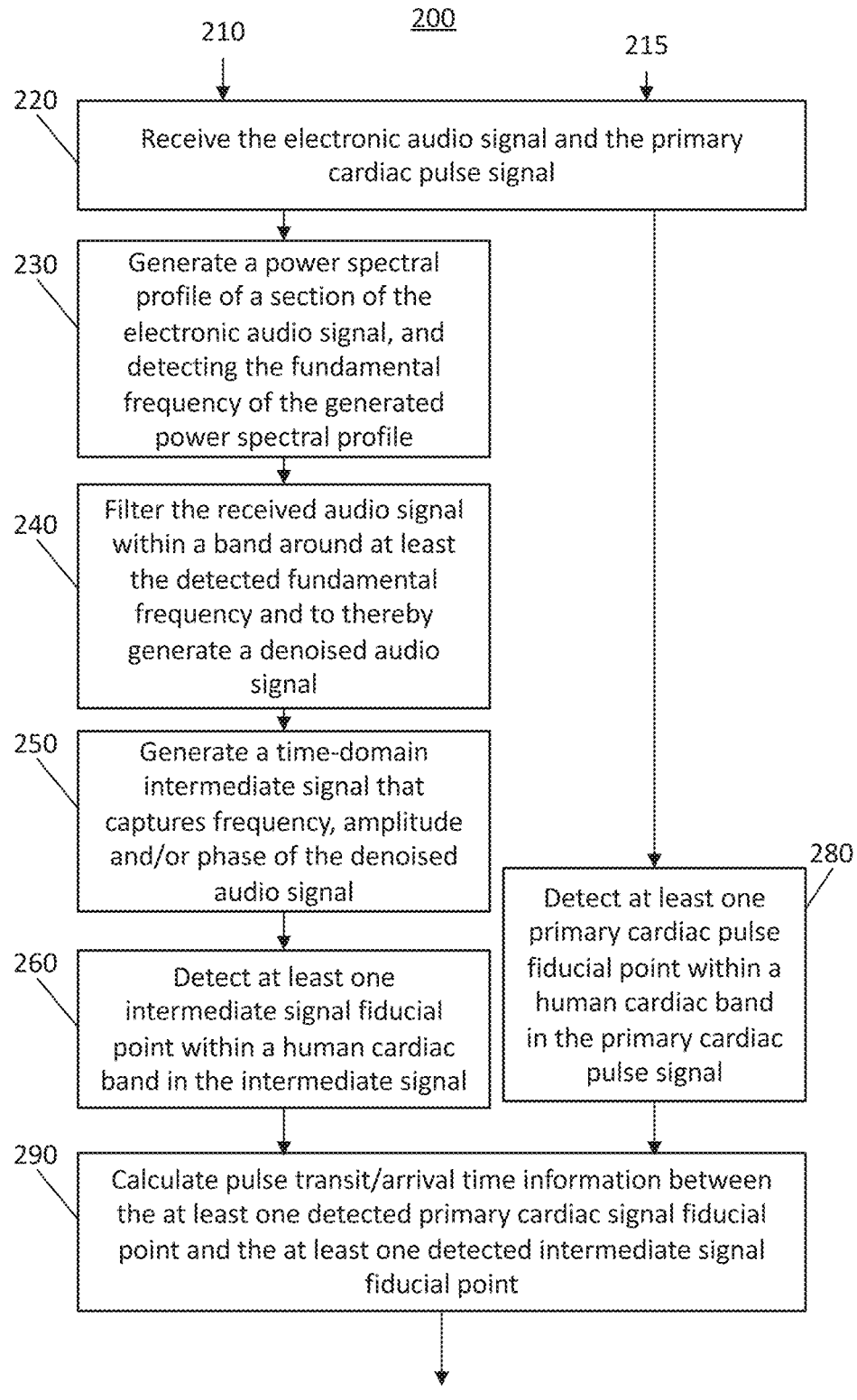
FIG. 6 shows a first example flow diagram for calculating cardiac pulse transit or arrival time information, in accordance with an embodiment.

FIG. 6 shows an example flow diagram 200 for calculating cardiac pulse transit/arrival time information of a subject, between a primary cardiac pulse signal 215 and an electronic audio signal 210. The method may be implemented in an electronic system or device, such as the ones described herein, or in a computer or processing unit. The electronic audio signal comprises information representative of a human voice signal in the time-domain, the human voice signal comprises a vowel audio sound of a certain duration and a fundamental frequency. The method comprises: at block 220, receiving the electronic audio signal and the primary cardiac pulse signal, wherein the electronic audio signal and the primary cardiac pulse signal are synchronized time-domain signals; at block 230, generating a power spectral profile of a section of the electronic audio signal, and detecting the fundamental frequency of the generated power spectral profile; at block 240, filtering the received audio signal within a band around at least the detected fundamental frequency and thereby generating a denoised audio signal 245; at block 250, generating a time-domain intermediate signal 255 that captures frequency, amplitude and/or phase of the denoised audio signal; at block 260, detecting at least one intermediate signal fiducial point 266 within a human cardiac band in the intermediate signal 255; at block 280, detecting at least one primary cardiac pulse fiducial point 286 within a human cardiac band in the primary cardiac pulse signal 215; and at block 290, calculating pulse transit/arrival time information 295 between the at least one detected primary cardiac signal fiducial point 286 and the at least one detected intermediate signal fiducial point 266.

According to example embodiments, the human cardiac band is around 40 to 200 bpm or 0.6 Hz to 3.5 Hz. According to example embodiments, the block 260 of detecting at least one intermediate signal fiducial point may comprise performing a bandpass filtering of the intermediate signal around a human cardiac band. According to example embodiments, the block 260 of detecting at least one intermediate signal fiducial point 266 comprises detecting fiducial points within a human cardiac band in the intermediate signal, on the time-domain. According to example embodiments, the block 260 of detecting at least one intermediate signal fiducial point 266 comprises extracting at least a time fiducial point from the intermediate signal 255, which is representative of the subject's heartbeat. According to some example embodiments, such detection of fiducial points may be based on peak detection in the signal or its derivatives, zero crossings, or other time-domain fiducial points. According to example embodiments, the block 260 of detecting at least one intermediate signal fiducial point comprises detecting a plurality of intermediate signal fiducial points, representative of beat by beat information of the subject's heartbeats.

According to example embodiments, the block 280 of detecting at least one primary cardiac pulse fiducial point may comprise performing a bandpass filtering of the primary cardiac pulse signal around a human cardiac band. According to example embodiments, the block 280 of detecting at least one primary cardiac pulse fiducial point comprises detecting fiducial points within a human cardiac band in the primary cardiac pulse signal, on the time-domain. According to example embodiments, the block 280 of detecting at least one primary cardiac pulse fiducial point comprises extracting at least a time fiducial point from the cardiac pulse signal 215, which is representative of the subject's heartbeat. According to some examples, when the cardiac pulse signal 215 is an ECG signal, the block 280 of detecting at least one primary cardiac pulse fiducial point comprises detecting one or more R peak fiducial points. According to some examples, when the cardiac pulse signal 215 is an ICG signal, the block 280 of detecting at least one primary cardiac pulse fiducial point comprises detecting one or more B fiducial points.

According to example embodiments, the block 290 of calculating pulse transit/arrival time information 295 comprises calculating a time difference between at least one detected primary cardiac signal fiducial point and at least one detected intermediate signal fiducial point corresponding to the same subject's heartbeat. According to example embodiments, the block 290 of calculating pulse transit/arrival time information 295 comprises receiving timing information about a plurality of detected fiducial points from the primary cardiac pulse reference signal and the intermediate signal and calculating timing differences (PTT/PAT)

for a plurality of the subject's heartbeats, e.g., one PTT/PAT value per beat. According to example embodiments, the block 290 of calculating pulse transit time information 295 comprises calculating statistically filtered (e.g., mean or median) PTT/PAT values.

According to example embodiments, the method 200 for calculating cardiac pulse transit/arrival time information comprises removing transition sections (e.g., start and end portions of the electronic audio signal) when calculating transit/arrival times. According to example embodiments, the method 200 for calculating cardiac pulse transit/arrival time information comprises accounting for and compensating any delays introduced by the electronic system while processing the electronic audio signal 10 and a primary cardiac pulse signal 15.

Figure 7A:
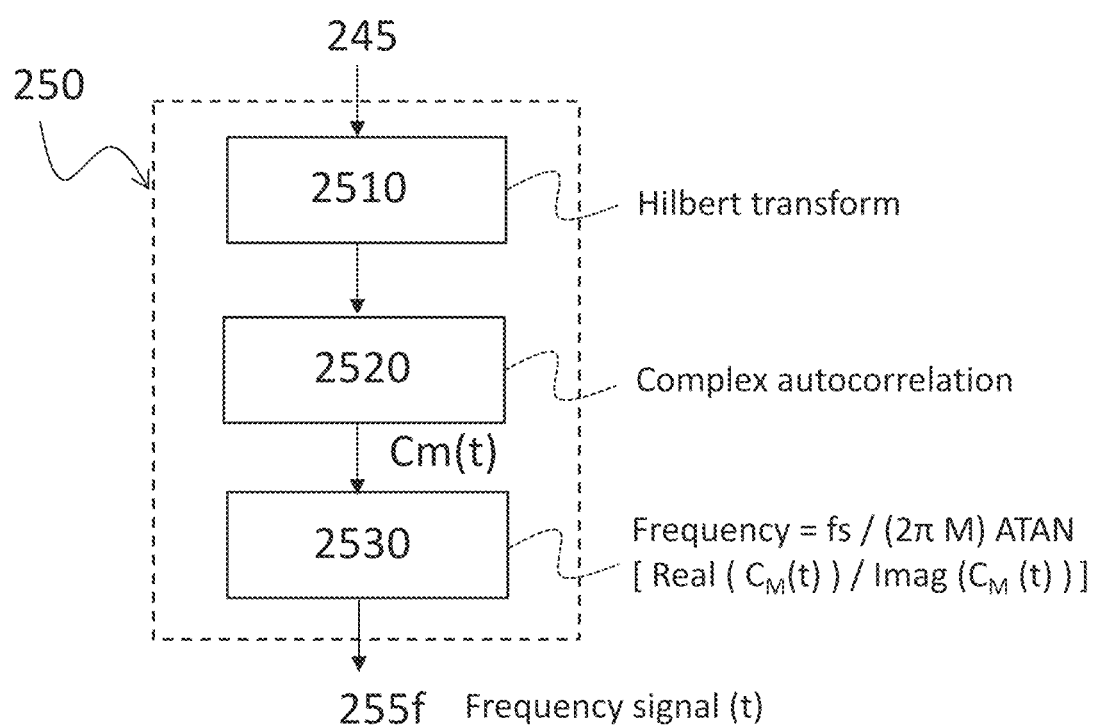
FIG. 7A shows a first example flow diagram for generating a time-domain intermediate signal that captures frequency information, in accordance with an embodiment.

FIG. 7A shows a first example flow diagram for the block 250 of generating a time-domain intermediate signal 255*f* that captures frequency information. The method comprises: at block 2510, calculating a Hilbert transform of the denoised audio signal 245; at block 2520, calculating a complex autocorrelation with M samples delay of the Hilbert transform; and at block 2530, calculating the instantaneous frequency.

Figure 7B:
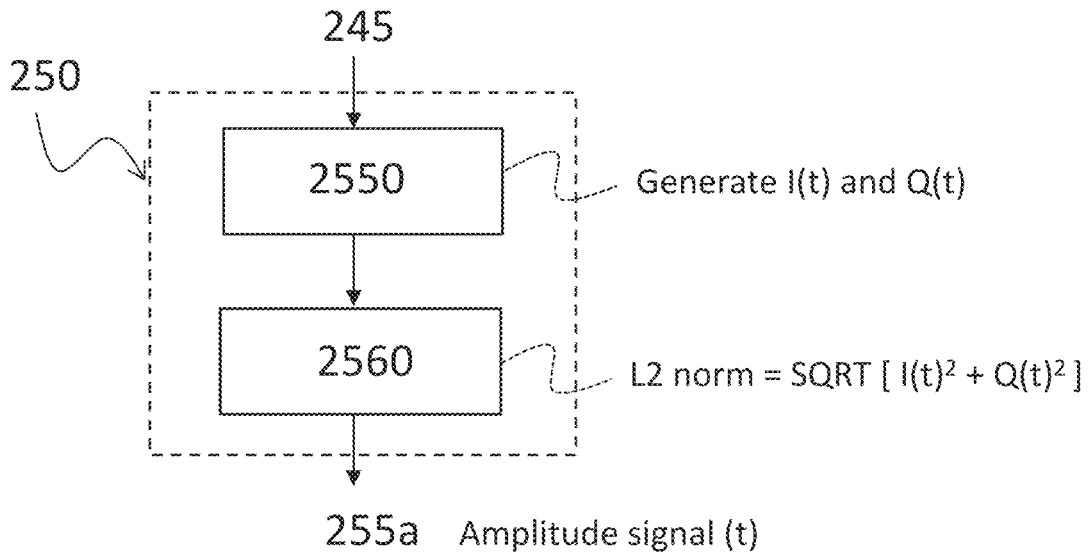
FIG. 7B shows a second example flow diagram for generating a time-domain intermediate signal that captures amplitude information, in accordance with an embodiment.

FIG. 7B shows a second example flow diagram for the block 250 of generating a time-domain intermediate signal 255*a* that captures amplitude information. The method comprises: at block 2550, generating an in-phase and a quadrature signal of the denoised audio signal 245, with a carrier having a frequency that is the fundamental frequency; and at block 2560, calculating the $L^2$ norm of the in-phase and quadrature signals.

Figure 7C:
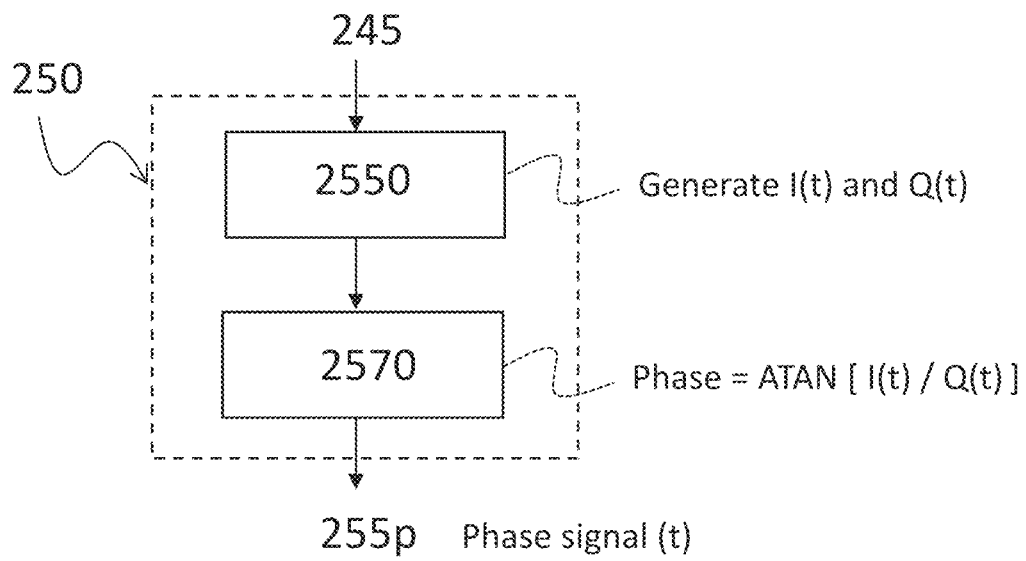
FIG. 7C shows a third example flow diagram for generating a time-domain intermediate signal that captures phase information, in accordance with an embodiment.

FIG. 7C shows a third example flow diagram for the block 250 of generating a time-domain intermediate signal 255*p* that captures phase information. The method comprises: at block 2550, generating an in-phase and a quadrature signal of the denoised audio signal, with a carrier having a frequency that is the fundamental frequency; and at block 2570, calculating the phase of the in-phase and quadrature signals.

Figure 8:
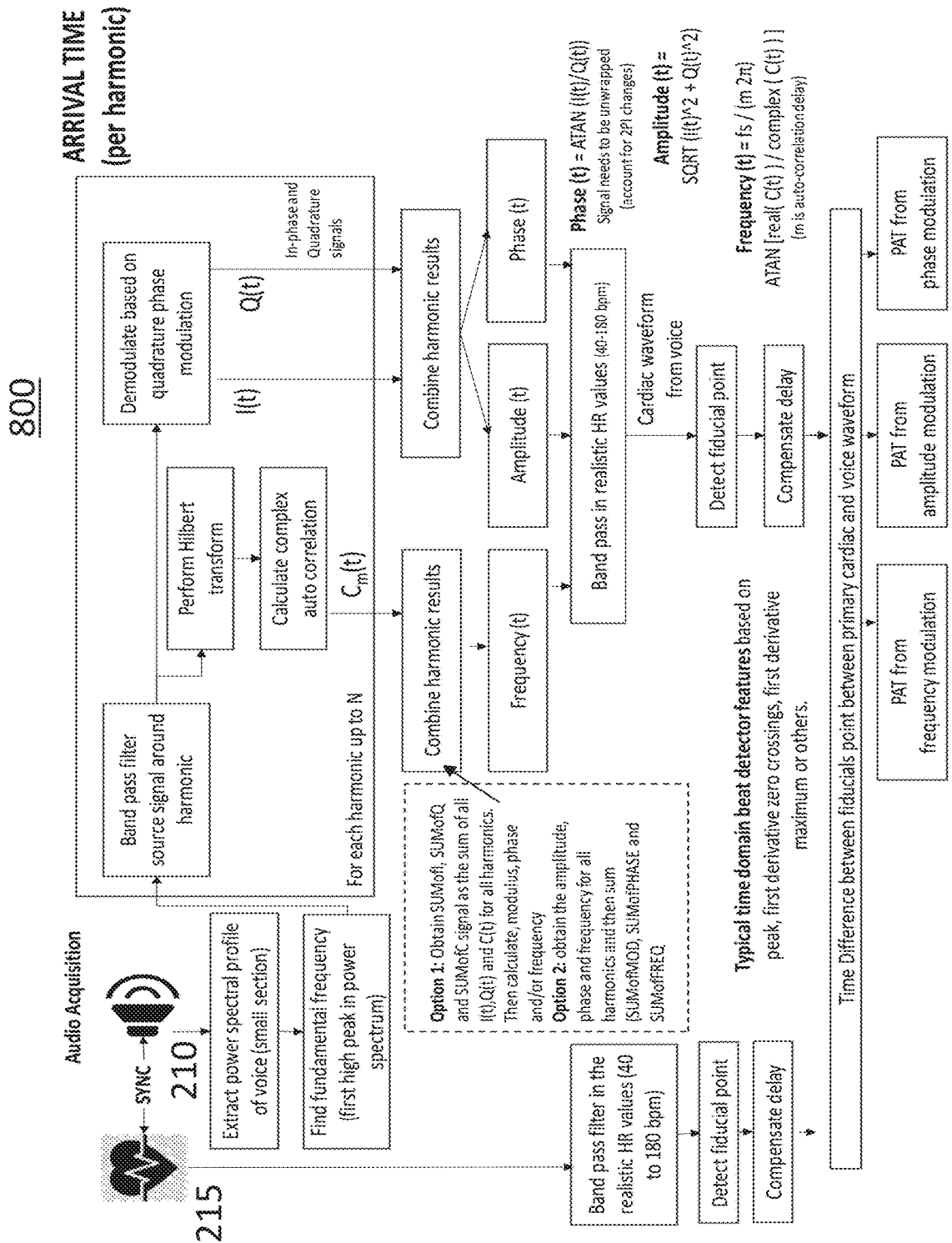
FIG. 8 shows a second example flow diagram for calculating cardiac pulse transit or arrival time information, in accordance with an embodiment.

FIG. 8 shows a second example flow diagram 800 for calculating cardiac pulse transit time information of a subject, from an electronic audio signal 210 and a primary cardiac pulse signal 215. According to an example embodiment, the electronic audio signal 210 may be generated by an audio acquisition module comprising a sensor (microphone), digitizer, and signal conditioning of the audio signal. The output of the acquisition is a digital audio signal at a voice like sample rate (in the kHz range). According to an example embodiment, the primary cardiac pulse signal 215 may be generated by a corresponding acquisition module comprising an analog front end and digitizing circuitry, resulting in a digital signal in the time-domain. The primary cardiac pulse signal is going to be used as a time reference for arrival time computation. According to example embodiments, the acquisition of the electronic audio signal 210 and the primary cardiac pulse signal 215 is performed under synchronization of both signal acquisition modules. According to example embodiments, the synchronization between the primary cardiac pulse signal and the electronic audio signal is performed in hardware, meaning that the digitizer circuits share the same clock. According to example embodiments, when each of the two digitizers receives a sample (or a reduced group of them), the digitizer also collects the timestamp, which has a common clock source in both of them. According to example embodiments, independent clocks may be used, and synchronization of the signals may be performed using software or other hardware means. According to example embodiments, the electronic audio signal 210 and the primary cardiac pulse signal 215 may be just stored on a memory or storage unit and read. According to embodiments, the electronic audio signal 210 and the primary cardiac pulse signal 215 may be just received by wired or wireless transmission means. According to an example embodiment, the method comprises extracting a power spectral profile of a small section of the electronic audio signal. According to embodiments, a small portion of the voice is extracted, and from it, a power spectral profile is computed. According to an example embodiment, the method comprises detecting the fundamental frequency of the voice signal from the power spectral profile. According to an embodiment, the first peak of the power spectral profile is the fundamental frequency. Based on the detection of the fundamental frequency, the subsequent harmonics should be at 2, 3, 4, etc., times the fundamental frequency. The method can be performed up to N harmonics. According to certain embodiments, the method is performed for N=4, as higher number of harmonics do not provide substantially better results but represent a higher computation expense. According to an example embodiment, for each of the harmonics until N, the method comprises:

1. Denoising the signal around the harmonic to reduce the sources of noise, e.g., typically +/−10 Hz around the Harmonic;
2a. Demodulating the signal following these steps
   Generating a Sine of the frequency of the Harmonic;
   Multiplying the filtered harmonic signal by the Sine, which results in the I(t) signal (In-phase);
   Optionally: Low pass filtering the I(t) signal to avoid aliasing
   Optionally: Downsampling the I(t) signal to a Cardiac-like (256 Hz for instance) sampling frequency;
   Generating a Cosine of the frequency of the Harmonic;
   Multiplying the filtered harmonic signal by the Cosine, which results in the Q(t) signal (Quadrature);
   Optionally: Low pass filtering the Q(t) signal to avoid aliasing;
   Optionally: Downsampling the Q(t) signal to a Cardiac-like (256 Hz for instance) sampling frequency.
2b. Performing complex autocorrelation, as an alternative or in addition to demodulation method 2a, following these steps:
   Calculating the Hilbert transform of the signal;
   Calculating the complex autocorrelation with m samples delay: $C_M(t)$;
   Calculating the phase, $\phi(t)$, of the complex autocorrelation signal, i.e., the arctangent of the real divided by the complex part of $C_M(t)$;
   Calculating the instantaneous frequency from the phase according to the following equation:

$f = fs*\phi(t)/(2\pi m)$, where $fs$ is sampling frequency;

Low pass filtering the Cm(t) signal to avoid aliasing;
   Optionally: Downsampling the Cm(t) signal to a cardiac-like (256 Hz for instance) sampling frequency.
3. Combining Harmonic results. The results from the harmonics need to be combined to generate a consolidated amplitude and phase signals. Two of the possible options for combination are the following:
   3.1 Option 1: summing all the results: get the sum of I(t) for all harmonics, and same for Q(t). Then compute the frequency, amplitude, and phase. Amplitude is the square root of the sum of the squares of I(t) and Q(t). Phase is the arctangent of I(t)/Q(t), which may be compensated by 2 pi shifts. Instantaneous frequency: calculate the phase, $\phi(t)$, of the complex autocorrelation signal, i.e., the arctangent of the real divided by the complex part of Cm(t). The instantaneous frequency (finst) is calculated from phase φ(t) according to the following equation:

finst=fs*φ(t)/(2πm), where fs is the sampling frequency.

3.2 Option 2: Calculating all amplitude and phase and sum: for each of the harmonics compute an amplitude and phase, sum the results.

Bandpass frequency, amplitude, and phase signals: the extracted frequency, amplitude, and phase modulations in the voice are filtered in the bandwidth of interest of Cardiac systems. This is roughly in the bandwidth corresponding to heart rates between 40 and 200 beats per minute. It is key that the filtering delay of the pulse needs to be controlled and accounted for, as it needs to be compensated.

According to an example embodiment, the method further comprises: optionally, performing a bandpass of the frequency, amplitude, and phase signals: the extracted frequency, amplitude and phase modulations in the voice are filtered in the bandwidth of interest of Cardiac systems. This is roughly in the bandwidth corresponding to heart rates between 40 and 200 beats per minute. When bandpass filtering is applied, the filtering delay of the pulse needs to be controlled and accounted for, as it needs to be compensated. This delay may also be accounted for by design or compensated during a configuration phase.

According to an example embodiment, the method further comprises: extracting frequency, amplitude, and phase relevant points from the signal related to heart beat information. According to an example embodiment, one or more time fiducial points are extracted from the amplitude and phase, which is characteristic of every beat in the signal. Such fiducial points can be based on peak detection in the signal or its derivatives, zero crossings, or other time-domain fiducial points. It should be characteristic for each of the beats.

According to an example embodiment, the method may further comprise filtering the primary cardiac pulse signal in the bandwidth of interest of cardiac systems. This is roughly in the bandwidth corresponding to heart rates between 40 and 180 beats per minute.

According to an example embodiment, the method further comprises extracting time fiducial points from the primary cardiac pulse, which is characteristic of every beat in the signal. For instance, in an ECG signal, this would be the R peak detector, or in an ICG signal the B point. Multiple options of fiducial points are possible for the multiple signals used as a time reference. The fiducial points found and its timing, referred to as the original clock are reported.

According to an example embodiment, the method further comprises correcting for any delay, e.g., filtering, up/down sampling, introduced in any stage by the system in the primary cardiac pulse and/or electronic audio signal paths.

According to an example embodiment, the method further comprises computing the differences between the timing of the fiducial points of the cardiac reference pulse signal and the timing of the fiducial points of the frequency, amplitude and phase signals. These differences may be calculated for every beat (one value per beat) and can be potentially statistically filtered (mean, median, etc.). According to an example embodiment, the method further comprises removing the transition sections of the voice (startup and end of recording) due to frequency variations. According to an example embodiment, the method calculates pulse arrival time from cardiac pulse to frequency modulated voice timing (per beat); pulse arrival time from cardiac pulse to amplitude-modulated voice timing (per beat); and/or pulse arrival time from cardiac pulse to phase-modulated voice timing (per beat).

Figure 9:
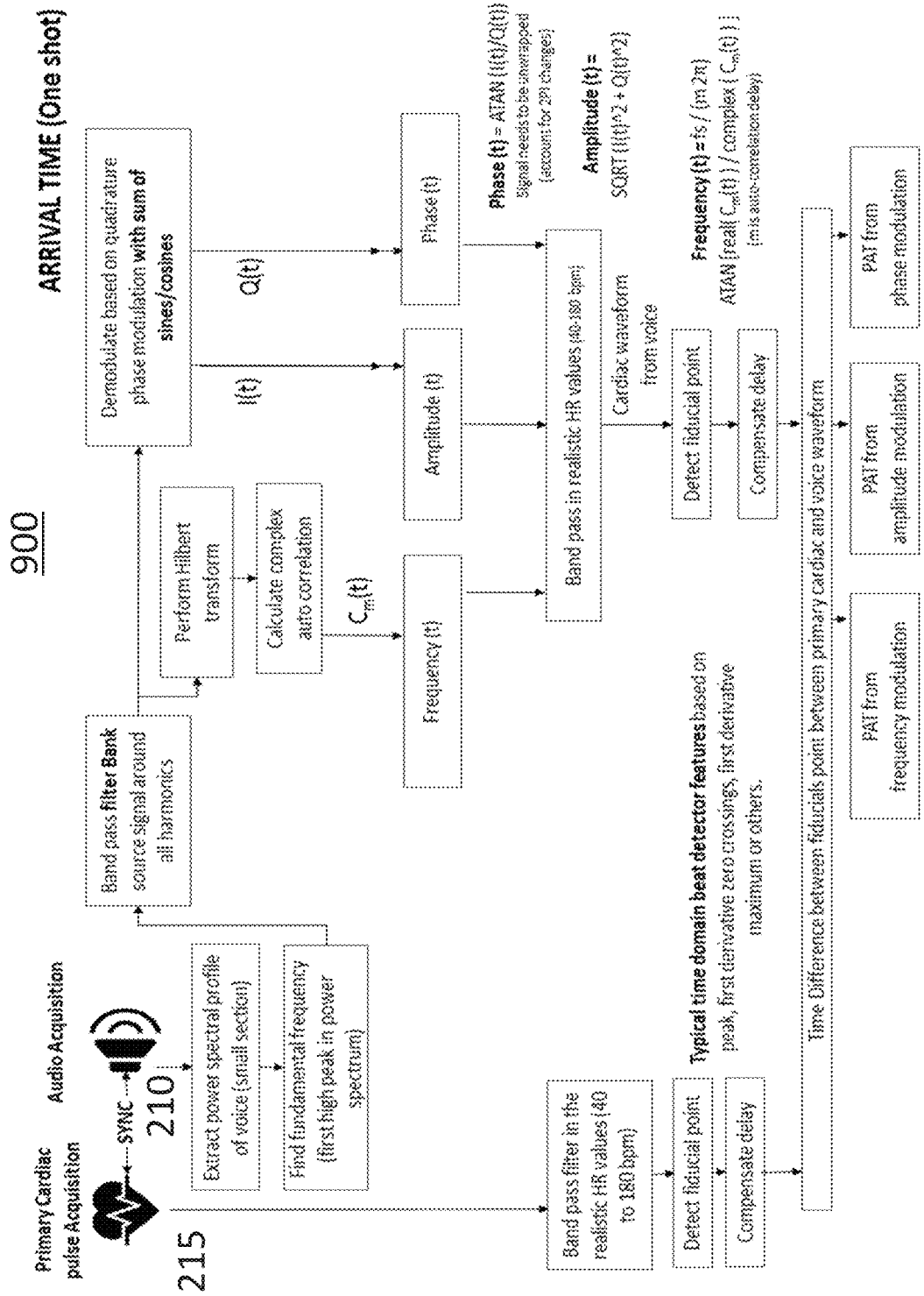
FIG. 9 shows a third example flow diagram for calculating cardiac pulse transit or arrival time information, in accordance with an embodiment.

FIG. 9 shows a third example flow diagram 900 for calculating cardiac pulse transit time information of a subject, from an electronic audio signal 210 and a primary cardiac pulse signal 215. According to an example embodiment, as an alternative to the block diagram per harmonic as shown in FIG. 8, the denoised audio signal can also be processed at once (not per harmonic as in FIG. 8). According to an example embodiment, the step of filtering the received audio signal within a band around at least the detected fundamental frequency and thereby generating a denoised audio signal 245, comprises performing multiple bandpass filters preserving the bandwidth around all the selected N harmonics (e.g., typically +/−10 Hz around each of the harmonics). This may be a composite filtering resulting from linearly combining filters for all the harmonics. According to an example embodiment, for the demodulation option, demodulating the signal by Generating a signal including the sum of sines of the first N harmonics according to the following equation:

x(t)=sin(2 pi f1)+sin(2 pi f2)+sin(2 pi f3)+ . . . .

Generating a signal including the sum of cosines of the first N harmonics according to the following equation:

y(t)=cos(2 pi f1)+cos(2 pi f2)+cos(2 pi f3)+ . . . .

Multiplying the filtered audio by x(t) to get I(t)
Multiplying the filtered audio by y(t) to get Q(t)

According to an example embodiment, for the complex autocorrelation: performing the Hilbert transform of the filtered signal containing all harmonics (instead of doing it per harmonic). The other processing steps are equal, as described above for FIG. 8.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

What is claimed is:

1. An electronic device including an electronic system configured to determine a subject's cardiac pulse transit time or pulse arrival time information, using a primary cardiac pulse signal and an electronic audio signal, wherein the electronic audio signal comprises information representative of a human voice signal in a time-domain, the human voice signal comprising a vowel audio sound of a certain duration and a fundamental frequency (F0); and wherein the electronic system comprises:

a signal receiving module configured to receive the electronic audio signal and the primary cardiac pulse signal, wherein the electronic audio signal and the primary cardiac pulse signal are synchronized time-domain signals;

an audio processing module configured to generate a power spectral profile of a section of the electronic audio signal, and to detect the fundamental frequency (F0) of the generated power spectral profile;

a denoising module configured to filter the received audio signal within a band around at least the detected fundamental frequency (F0) to thereby generate a denoised audio signal;

a signal transformation module configured to generate a time-domain intermediate signal that captures one or more of: a frequency, an amplitude, or a phase of the denoised audio signal;

a beat detection module configured to detect at least one intermediate signal fiducial point, within a human cardiac band, in the intermediate signal;

a primary cardiac pulse beat detection module configured to detect at least one primary cardiac pulse fiducial point, within a human cardiac band, in the primary cardiac pulse signal; and a cardiac pulse transit/arrival time module configured to generate an estimation of arterial blood pressure based on the pulse transit time or pulse arrival time information between the at least one detected primary cardiac pulse fiducial point and the at least one detected intermediate signal fiducial point.

2. The system according to claim 1, wherein the signal transformation module is configured to receive the denoised audio signal and calculate a Hilbert transform; a complex autocorrelation with M samples delay; and an instantaneous frequency, to thereby generate a time-domain intermediate signal that captures the frequency of the denoised audio signal.

3. The system according to claim 2, wherein the signal transformation module is configured to generate an in-phase (I) and quadrature (Q) signal of the denoised audio signal, with a carrier having a frequency that is the fundamental frequency (F0); and calculate an $L^2$ norm of the in-phase and quadrature signals, thereby generating a time-domain intermediate signal capturing the amplitude of the denoised audio signal.

4. The system according to claim 2, wherein the signal transformation module is configured to generate an in-phase (I) and quadrature (Q) signal of the denoised audio signal, with a carrier having a frequency that is the fundamental frequency (F0); and calculate the phase of the in-phase and quadrature signals, thereby generating a time-domain intermediate signal capturing the phase of the denoised audio signal.

5. The system according to claim 2, wherein the denoising module is further configured to filter the received audio signal also within bands around one or more multiples of the detected fundamental frequency (F0) and to generate one or more denoised audio signals.

6. The system according to claim 1, wherein the signal transformation module is configured to generate an in-phase (I) and quadrature (Q) signal of the denoised audio signal, with a carrier having a frequency that is the fundamental frequency (F0); and calculate an $L^2$ norm of the in-phase and quadrature signals, to thereby generate a time-domain intermediate signal that captures the amplitude of the denoised audio signal.

7. The system according to claim 6, wherein the signal transformation module is configured to generate an in-phase (I) and quadrature (Q) signal of the denoised audio signal, with a carrier having a frequency that is the fundamental frequency (F0); and calculate the phase of the in-phase and quadrature signals, to thereby generate a time-domain intermediate signal that captures the phase of the denoised audio signal.

8. The system according to claim 6, wherein the denoising module is further configured to filter the received audio signal also within bands around one or more multiples of the detected fundamental frequency (F0) and to generate one or more denoised audio signals.

9. The system according to claim 1, wherein the signal transformation module is configured to generate an in-phase (I) and quadrature (Q) signal of the denoised audio signal, with a carrier having a frequency that is the fundamental frequency (F0); and calculate the phase of the in-phase and quadrature signals, to thereby generate a time-domain intermediate signal that captures the phase of the denoised audio signal.

10. The system according to claim 9, wherein the denoising module is further configured to filter the received audio signal also within bands around one or more multiples of the detected fundamental frequency (F0) and to generate one or more denoised audio signals.

11. The system according to claim 1, wherein the denoising module is further configured to filter the received audio signal also within bands around one or more multiples of the detected fundamental frequency (F0) and to generate one or more denoised audio signals.

12. The system according to claim 11, wherein the denoising module is configured to generate a plurality of denoised audio signals and the signal transformation module is configured to combine calculation results from each of the denoised audio signals.

13. A method implemented by an electronic system or device for determining cardiac pulse transit time or pulse arrival time information of a subject using a primary cardiac pulse signal and an electronic audio signal, wherein the electronic audio signal comprises information representative of a human voice signal in a time-domain, the human voice signal comprising a vowel audio sound of a certain duration and a fundamental frequency (F0), and the method comprising:

receiving the electronic audio signal and the primary cardiac pulse signal, wherein the electronic audio signal and the primary cardiac pulse signal are synchronized time-domain signals;

generating a power spectral profile of a section of the electronic audio signal;

detecting the fundamental frequency (F0) in the generated power spectral profile;

filtering the received audio signal within a band around at least the detected fundamental frequency (F0) and thereby generating a denoised audio signal wherein filtering the received audio signal within the band includes within bands around one or more multiples of the detected fundamental frequency (F0) and to generate one or more denoised audio signals;

generating a time-domain intermediate signal that captures one or more of: a frequency, an amplitude, or a phase of the denoised audio signal; and detecting at least one intermediate signal fiducial point within a human cardiac band in the intermediate signal;

detecting at least one primary cardiac pulse fiducial point within a human cardiac band in the primary cardiac pulse signal; and generating an estimation of arterial blood pressure based on the pulse transit time or pulse arrival time information between the at least one detected primary cardiac pulse fiducial point and the at least one detected intermediate signal fiducial point.

14. The method according to claim 13, wherein generating a time-domain intermediate signal that captures the frequency of the denoised audio signal comprises: calculating a Hilbert transform; calculating a complex autocorrelation with M samples delay; and calculating an instantaneous frequency.

15. The method according to claim 14, wherein generating a time-domain intermediate signal that captures the amplitude of the denoised audio signal, comprises: generating an in-phase (I) and a quadrature (Q) signal of the denoised audio signal, with a carrier having a frequency that is the fundamental frequency (F0); and calculating an $L^2$ norm of the in-phase and quadrature signals.

16. The method according to claim 13, wherein generating a time-domain intermediate signal that captures the amplitude of the denoised audio signal, comprises: generating an in-phase (I) and a quadrature (Q) signal of the denoised audio signal, with a carrier having a frequency that is the fundamental frequency (F0); and calculating an $L^2$ norm of the in-phase and quadrature signals.

17. The method according to claim 13, wherein generating a time-domain intermediate signal that captures the phase of the denoised audio signal, comprises: generating an in-phase (I) and a quadrature (Q) signal of the denoised audio signal, with a carrier having a frequency that is the fundamental frequency (F0); and calculating the phase of the in-phase and quadrature signals.

18. A computer program product comprising computer program code that facilitates calculating cardiac pulse transit time or pulse arrival time information of a subject according to the method of claim 13 when the program is run on a computer.

19. A non-transitory computer-readable storage medium comprising a computer program according to claim 18.

* * * * *